（12） United States Patent
Dunn et al.

(10) Patent No.: US 7,792,419 B2
(45) Date of Patent: Sep. 7, 2010

(54) ILLUMINATOR-ESPECIALLY FOR CYLINDRICAL CURVED SURFACES

(75) Inventors: Sheila Bergeron Dunn, Mason, NH (US); Joseph Marcel La Flamme, New Boston, NH (US); Michael C. Messina, Hooksett, NH (US); Michael Zielinski, Candia, NH (US)

(73) Assignee: Microscan Systems, Inc., Renton, WA (US)

( * ) Notice: Subject to any disclaimer, the term of this patent is extended or adjusted under 35 U.S.C. 154(b) by 880 days.

(21) Appl. No.: 11/591,343

(22) Filed: Nov. 1, 2006

(65) Prior Publication Data

US 2007/0097686 A1 May 3, 2007

(51) Int. Cl.
*G03B 15/02* (2006.01)
(52) U.S. Cl. .......................................... 396/4
(58) Field of Classification Search ....................... 396/4, 396/155, 182; 362/3, 11, 16
See application file for complete search history.

(56) References Cited

U.S. PATENT DOCUMENTS

| 5,175,428 | A | | 12/1992 | Agerskov et al. | ........... | 250/223 |
| 5,842,060 | A | * | 11/1998 | White et al. | ............... | 396/155 |
| 6,270,338 | B1 | * | 8/2001 | Eroglu et al. | ................. | 431/8 |
| 6,749,310 | B2 | * | 6/2004 | Pohlert et al. | ................ | 362/11 |

FOREIGN PATENT DOCUMENTS

| GB | 2057675 | 4/1981 |
| GB | 2155630 | 3/1985 |
| GB | 2249169 | 4/1992 |
| JP | 2004085204 | 3/2004 |
| WO | WO97/00438 | 1/1997 |

OTHER PUBLICATIONS

PCT Search Report—PCT/US2006/042865—mailed Mar. 8, 2007.

* cited by examiner

*Primary Examiner*—W. B. Perkey
(74) *Attorney, Agent, or Firm*—Blakely Sokoloff Taylor & Zafman LLP

(57) ABSTRACT

A plurality of LED's, or electro luminescent strips, are disposed to project illumination to and thru, or towards, a diffuser; resulting in at least a portion of generated diffuse illumination being directed towards and upon the cylindrical surface of an article or part when disposed at an article illumination location. The article illumination location is established so that a centerline through the article is co-linear with a center line of the diffuse illumination projecting from, or reflected from, the diffusers. A housing may be provided for the LED's, electro luminescent strips and diffusers; or they may be otherwise arranged to coact to provide diffuse illumination directed towards the cylindrical surface of the part or other article. illumination reflected off of the article's cylindrical surface, and/or any markings, such as symbology, carried thereby is directed to a lens/camera arrangement to provide an image of same for transmission to a computer, controller, smart camera or other image utilization system.

17 Claims, 5 Drawing Sheets

ILLUMINATOR-ESPECIALLY FOR CYLINDRICAL CURVED SURFACES

BACKGROUND OF THE INVENTION

1. Field of Application

This invention relates to illumination of curved surfaces; and more particularly to illumination of round, reflective, cylindrical parts of curved surfaces.

2. Description of the Prior Art

It is often necessary in Machine Vision to light or illuminate round, reflective, cylindrical parts of curved surfaces evenly enough to read date and lot codes and other symbology such as data matrix marks, or to be able to inspect such parts for flaws like: gouges; dents; scratches; etc. Some illumination devices, particularly those commonly referred to as continuous diffuse illuminators (CDI): are shown, and described, by way of example in U.S. Pat. No. 5,461,417 patented to T. P. White, et al on Oct. 24, 1998 for "Continuous Diffuse Illumination Method and Apparatus". Other similar illuminators are shown and described, for example, in other ones of U.S. Patents to T. P. White under U.S. Pat. Nos. 5,539,485; 5,604,550; 5,684,530; and 5,713,661 respectively.

Other CDI's, and quoted light sources, that may provide uniform illumination of curved surfaces typically require a complex structure of multiple lighting sources and optical elements like beamsplitters, reflecting domes and light blocks. They may also dictate a rigid camera location.

SUMMARY OF THE INVENTION

The present invention provides illuminators for cylindrical curved surfaces that illuminate the curved surface evenly.

The present invention provides illuminators for cylindrical curved surfaces that illuminate the curved surface evenly with respect to a viewing camera.

The present invention provides illuminators for cylindrical curved surfaces that illuminate the curved surface evenly with respect to a viewing camera while still maintaining a brightfield viewing effect.

The present invention provides illuminators for cylindrical curved surfaces that illuminate the curved surface evenly with respect to a viewing camera while facilitating flexible and non complex mounting of the camera and/or cameras while allowing some flexibility in camera positioning.

The present invention provides illuminators that provide a relatively wide semicircle of diffused light with uniform lighting to cover up to 180 degrees of a surface such that light rays reflect off that surface and back to a camera/lens combination and result in a uniform "even" image.

The present invention provides illuminators for cylindrical curved surfaces that illuminate the curved surface evenly, are relatively of low cost, and have a relatively small footprint.

The present invention provides illuminators that eliminate the need for items such as dual light sources, beam splitters, reflecting domes and light blocks otherwise used in CDI's.

The present invention provides methods to facilitate illumination of cylindrical curved surfaces and to evenly illuminate the curved surface.

Other features and advantages of the invention in its details of construction and arrangement of elements and systems will be seen from the above and from the following description of the preferred embodiments when considered in conjunction with the accompanying drawings and appended claims.

BREIF DESCRIPTION OF THE DRAWINGS

DESCRIPTION OF THE INVENTIVE EMBODIMENTS

Figure 1A:
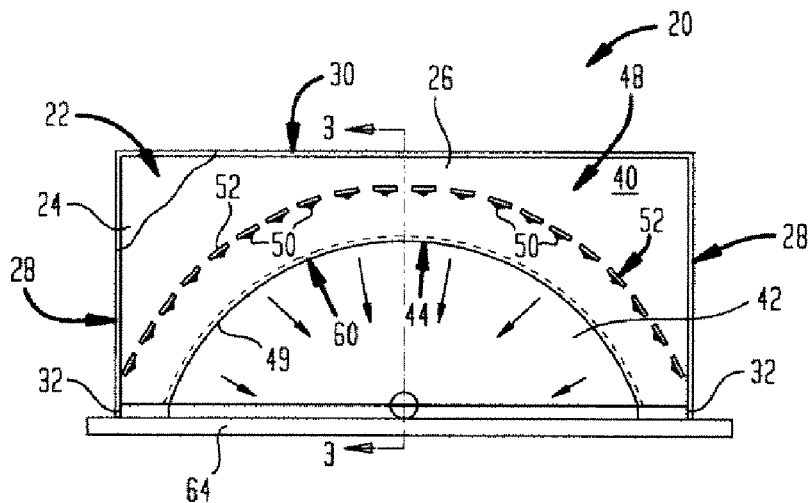
FIG. 1A is an elevation view of a face an end view of an illuminator, incorporating the instant invention, positioned over a cylindrical curved part
Figure 1B:
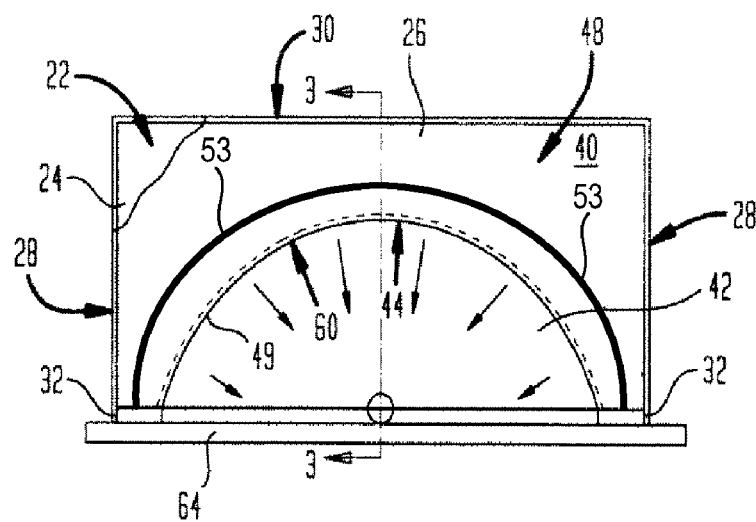
FIG. 1B is an elevation view of a face an end view of an alternative embodiment an illuminator, incorporating the instant invention, positioned over a cylindrical curved part.
Figure 2:
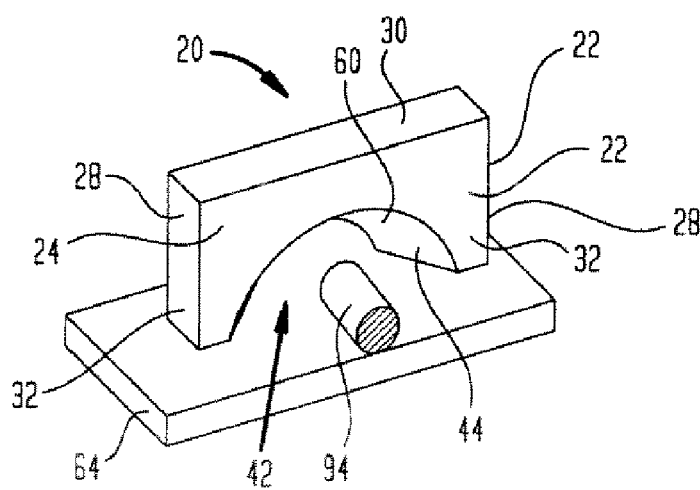
FIG. 2 is an isometric sketch of the illuminator and cylindrical part of FIG. 1.

With respect to FIGS. 1 and 2 there is shown at 20 an illuminator incorporating the instant invention and including a housing 22 fabricated with a front panel 24 , a rear panel 26 (FIG. 1), a pair of spaced side panels 28 (FIGS. 1 & 2), a top panel 30, and a pair of spaced bottom legs 32 (FIG. 1). All assembled together to provide an interior space 40. Front panel 24 and rear panel 26 are each substantially rectangular and each includes a semi-circular section 42, extending from an edge into the panel, removed therefrom, to provide a semi-circular curved edge surface 44 thereon. When housing 22 is assembled the edges of the front panel 24 and rear panel 26 is disposed so that sections 42 and semi-circular curved edges 44 are aligned. Sections 42 may be removed from substantially rectangular panels from which front panel 24 and rear panel 26 are formed or may be otherwise fabricated.

An illumination source 48, in this instance consisting of a plurality of LED's 50 is provided for illuminator 20. LED's 50 are disposed within interior space 40 of housing 22. LED's 50 are mounted in spaced relationship, in strip-like configuration, on a suitable backing or support (not shown) that is conventionally secured within interior space 40 of housing 22 so that LED's 50 are arranged in a semi-circular array along an arc circle 52 (FIG. 1A), substantially parallel to curved edge surfaces 44, but spaced into and within housing 22 from edge surfaces 44. Alternatively an electro luminescent strip 53 (FIG. 1B) may be utilized as the illumination source instead of the array of LED's 50. Suitable and conventional electrical connections (not shown) are provided for LED's 50 to connect it for use and to connect LED's 50 to a suitable and conventional source of power.

A diffuser 60, of substantially conventional material, is disposed between front panel 24 and rear panel 26 proximate edge surfaces 44 thereof and so as to receive illumination from LED's 50 and diffuse such illumination.

When illuminator 20 is to be used, housing 22 is placed upon a suitable surface, such as a table or workbench top 64 (FIGS. 1-4) and a part to be imaged is either placed on top 64 or a suitable part holder 66. The illumination from LED's 50 first passes through diffuser 60 and upon passing through diffuser 60 is diffused thereby. The resulting diffuse illumination 78 (FIG. 3) emanates in all directions. A sufficient portion 80 of illumination 78, however, is projected towards and onto cylindrical surface 68 of part 70, pr other article, when the center axis of part, or other article,70 is co-linear with a center line 74 of arc circle 52 along which LED's 50 are disposed.

An image capture arrangement 86 (FIG. 3), which includes at least a lens 88 and a camera 90 is disposed and suitably mounted to receive light rays 92 reflected from cylindrical surface 68 of part 70. Light rays 92 are thus directed to camera 90 for further use and interpretation by conventionally available programs and equipment. Suitable and conventional electrical circuitry connects the lens/camera combination arrangement to a computer or controller (not shown) with software to decode or otherwise utilize the output of the lens/camera combination arrangement.

Figure 3:
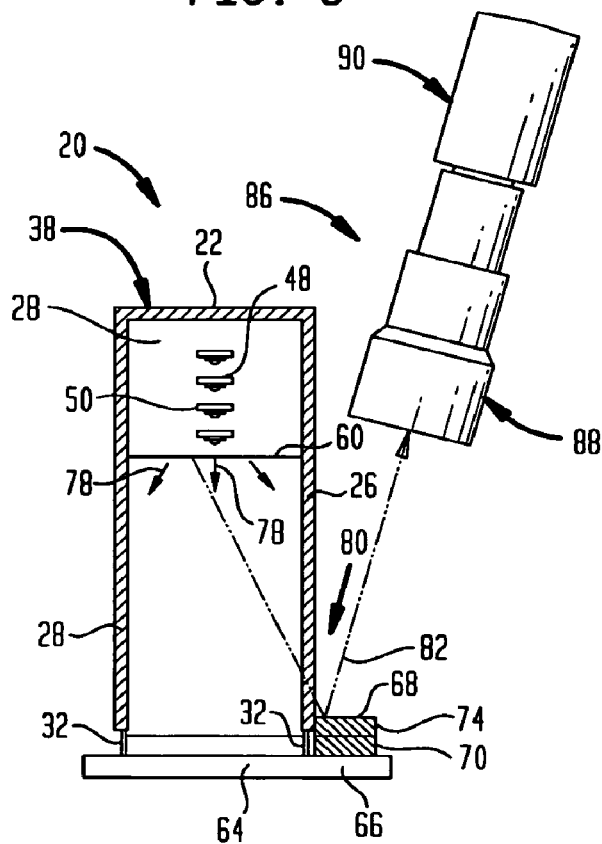
FIG. 3 is a side elevation view, in partial section of the illuminator and cylindrical part, taken on line 3-3, of FIG. 1, enlarged to better show details thereof and with a lens and camera schematically disposed to receive a reflection from the cylindrical part when illuminated.
Figure 4:
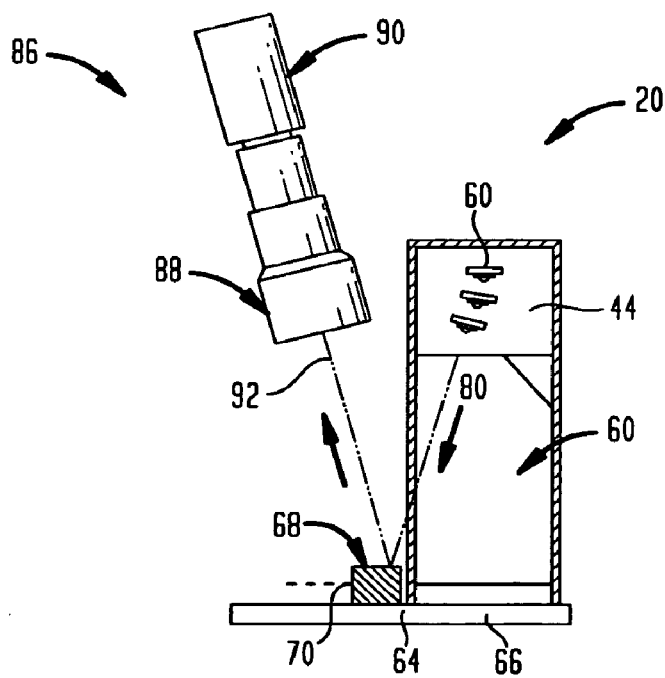
FIG. 4 is a side elevation view of the illuminator and cylindrical part of FIG. 3 reversed with respect to the showing in FIG. 3.

The above described illuminator 20 and image capture arrangement 86 provide a uniform lighting 78, 80, 82 to cover up to 180 degrees (180°) of the surface 68 of a part, or other article, 70 such that light rays 82 reflect off part 70 and back to the camera/lens combination 90/88 resulting in a uniform, "even" image. Maintaining a diffused brightfield which results in, 1) a high contrast between any symbology, such as a date code or data matrix 94 (FIG. 2) when disposed on surface 68 of part 70, and cylindrical surface 68 of part 70; and 2) elimination of unwanted specular reflections. This illumination offers a wide semicircle of diffused light and can be situated just off to the side of the target or also just above the target. The image capture arrangement 86 is to be positioned such that light 82 is reflected to camera 90 at the same angle as the incident light (FIG. 3). Because the illumination surface is wide and diffused, this angle has a degree of variability allowing some flexibility in camera positioning while still maintaining the brightfield lighting effect.

The resulting illumination from illuminator 20 will provide the widest possible solid angle of illumination, about 180° along the circumference of part 70. If the distance between the illuminator and part or article is increased, the solid angle of illumination will decrease. This will illuminate less of the target's curved surface, but will still be suitable for certain applications. Diffuse illumination from illumination source 48 is to be directed to a center line through an article or part at a center line of the arc circle of the illumination source and, as such, will properly illuminate the curved circular surface of the article or part.

Illuminator 20 achieves a small footprint by virtue of its arch like shape which illuminates the target through up to 180° of its curved axis. It avoids the excess illuminated area that would be required to illuminate additional planes (e.g. cylinder ends or a spherical object). This arch shape provides a reduction in overall dimensions for illuminators designed to address targets with curved surfaces. Therefore, illuminator 20 eliminates and renders unnecessary items such as dual light sources, beam splitters, reflecting domes and light blocks otherwise present in conventionally available CDI's.

Illuminator 20 relies on an assortment of LEDs or other distributed light sources placed along an arch behind a curved diffuser so as to evenly dissipate light. As the resulting diffused light illuminates the cylinder surface very evenly, any aberration of the surface by print, deposit or indentation will reflect light away from the eye of the camera and will show as a darker element along the surface. This will provide the contrast necessary for the vision algorithms to decipher the characters and or to identify imperfections. Since the camera and lens combination can be totally independent from the illumination, many different cameras and computer configurations can be used including "smart cameras".

Figure 5:
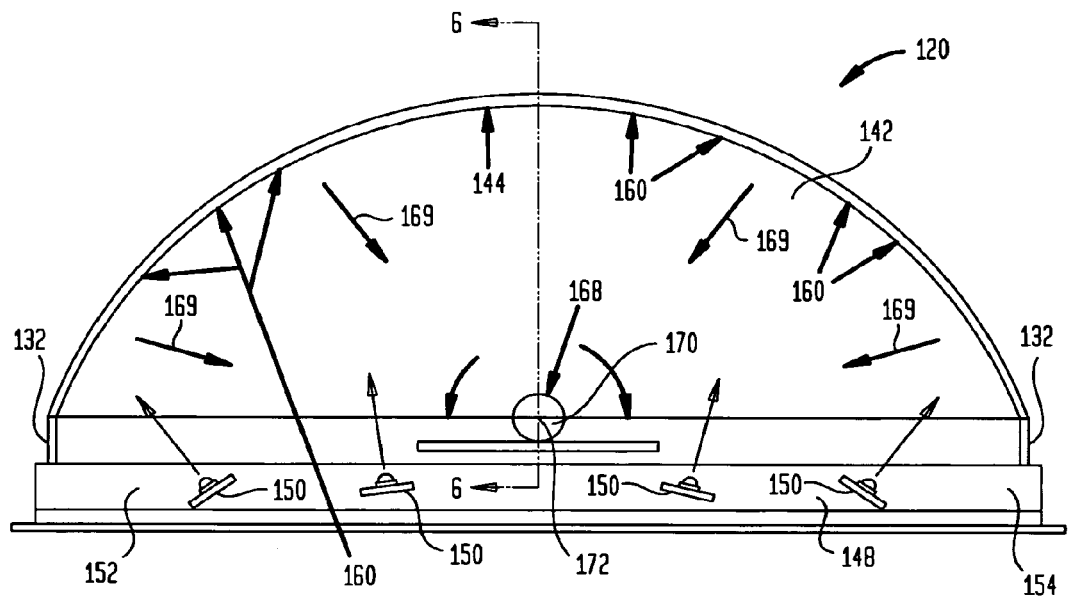
FIG. 5 is a front elevation view of an alternative embodiment of illuminator, incorporating the instant invention, with a cylindrical part schematically shown to be illuminated thereby.
Figure 6:
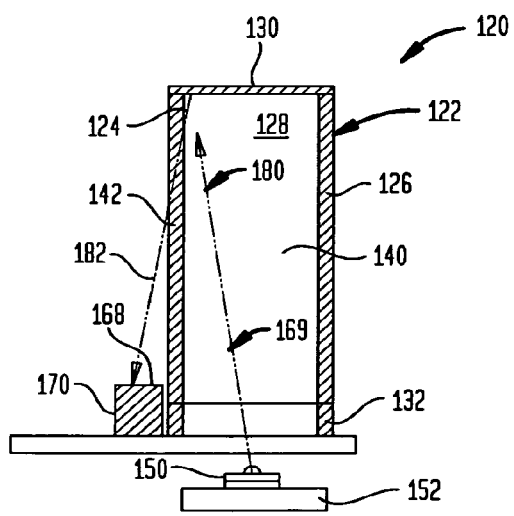
FIG. 6 is a side elevation view, in partial section, of the illuminator and cylindrical part, taken on line 6-6, of FIG. 5, with a lens and camera schematically disposed to receive a reflection from the cylindrical part when illuminated.

With respect to FIGS. 5 and 6 there is shown at 120 an alternate embodiment of illuminator, incorporating the instant invention, and including a housing 122 (FIG. 5) fabricated in a manner similar to housing 20 of the embodiment of FIGS. 1-3. Housing 122 includes a front panel 124, a rear panel 126, a pair of spaced side panels 128 a top panel 130, and a pair of spaced bottom legs 132 all assembled together to provide an interior space 140. Front panel 124 and rear panel 126 are each substantially rectangular and each includes a semi-circular section 142 (FIG. 5) similar to section 42 of the FIGS. 1-3 embodiment, extending from an edge into the panel removed therefrom to provide a semi-circular curved edge surface 144 (FIG. 5). When housing 122 is assembled the edges of the front panel 124 and rear panel 126 is disposed so that sections 142 and semi-circular curved edges 144 are aligned. Sections 142 may be removed from substantially rectangular panels from which front panel 124 and rear panel 126 is formed or may be otherwise fabricated.

An illumination source 148, in this instance consisting of a plurality of LED's 150 is provided for illuminator 120. LED's 150 are suitably carried by an illumination carrier 152 to be disposed either within an illumination space 154 of carrier 152 of housing 122; or as a fabrication separate from housing 122 but fabricated to be disposed beneath housing 122 as shown in FIGS. 5 and 6. LED's 150 are mounted in spaced relationship, in strip-like configuration, on a suitable backing or support (not shown) that is conventionally secured within interior space 154 of carrier 152. LED's 150 are each arranged so that their respective illuminations are directed towards one or more diffuse reflectors 160, suitably secured within housing 122, to receive such illumination and reflect diffuse illumination 169 towards the surface 168 of a part, or other article, 170 disposed at a center axis 172 of opening edge 144. Alternatively an electro luminescent strip (not shown) may be utilized as the illumination source instead of the array of LED's 150. Suitable and conventional electrical connections (not shown) are provided for LED's 150 and/or electro luminescent strip to connect it for use and to connect it to a suitable and conventional source of power; as well as for a suitable and conventional lens/camera combination similar to that shown and described for the embodiment of FIGS. 1-3 and to a computer, controller or to a "smart camera".

In the FIGS. 5 and 6 embodiment illumination 180 is directed to and impinge upon diffuse reflectors 160 and at least a portion of the diffuse illumination 182 reflected therefrom impinges upon cylindrical surface 168 of part 170 and therefrom to an image capture arrangement as shown and described above for the embodiment of FIGS. 1-3.

Figure 7:
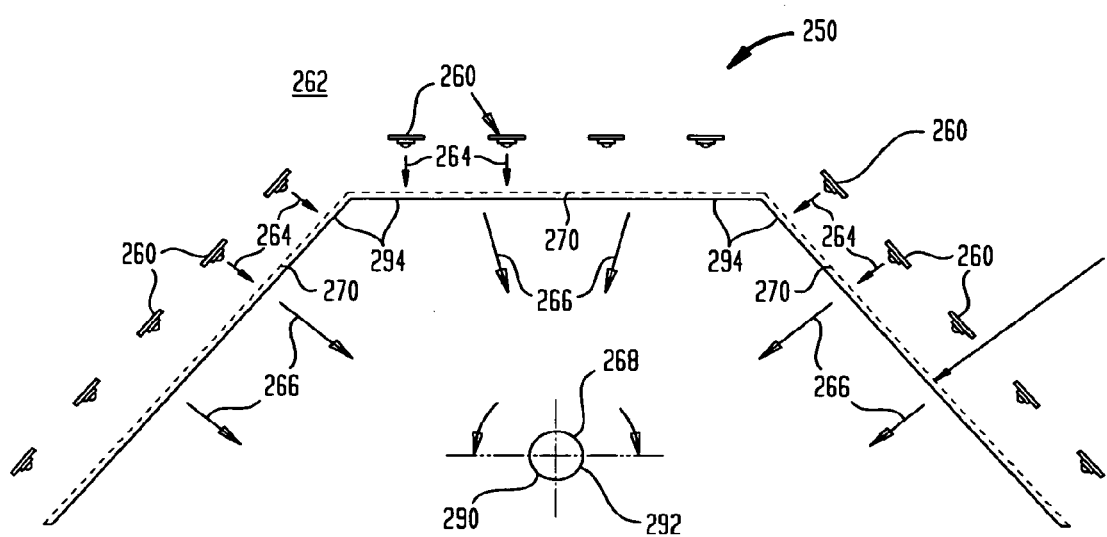
FIG. 7 is a front elevation view of an alternative embodiment of illuminator, incorporating the instant invention, with a cylindrical part schematically shown to be illuminated thereby.
Figure 8:
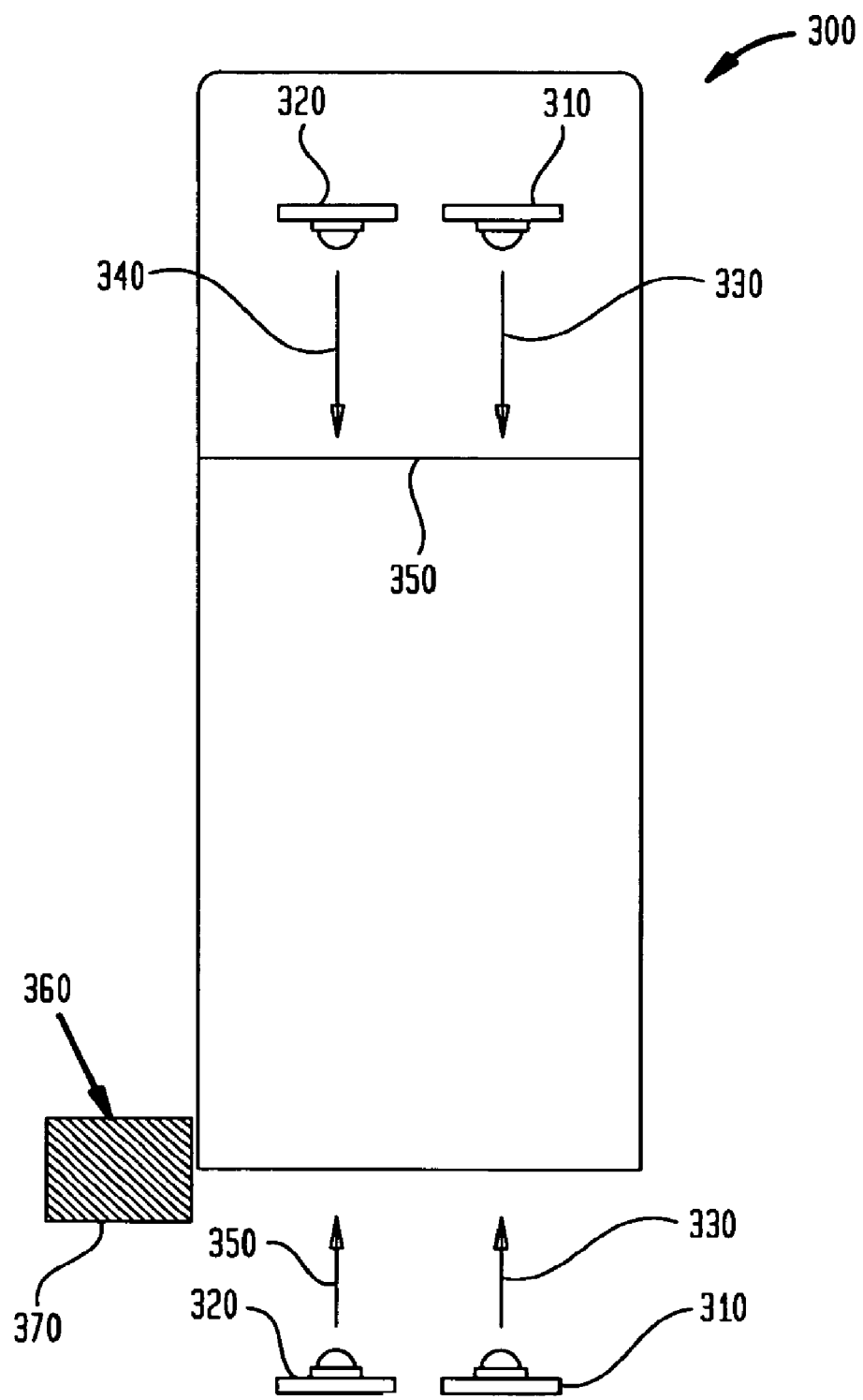
FIG. 8 is a side elevation view, in partial section, of yet another embodiment of illuminator incorporating the instant invention.

With respect to FIG. 7 there is shown at 250 an alternative illumination source including a plurality of LED's 260 suitably carried by an illumination carrier 262 and disposed within a housing similar to housing 22 of the embodiment of FIGS. 1-3. LED's 260 are mounted in spaced relationship, as shown in FIG. 7, and in strip-like configuration, on a suitable backing or support (not shown) that is conventionally secured within an interior space of the housing. LED's 260 are, furthermore, disposed and arranged so that their respective illuminations 264 are directed towards one or more diffusers 270 suitably secured within the housing to receive such illumination. Diffusers 270, in turn, permit projection of diffuse illumination 266 towards the surface 288 of a part, or other article, 290 disposed at a center axis 292 of an opening 294 of the housing. Alternatively an electro luminescent strip (not shown) may be utilized as the illumination source instead of the array of LED's 260. Suitable and conventional electrical connections (not shown) are provided for LED's 260 and/or electro luminescent strip to connect them for use and to connect them to a suitable and conventional source of power.

It should be noted that in the embodiment of FIG. 7 the housing opening is formed by relatively straight edges 294 configured and positioned to correspond to the configuration and layout of LED's 260, or alternatively the electro luminescent strip. Furthermore in the FIG. 7 embodiment at least a portion of the diffuse illumination 266 impinges upon cylindrical surface 288 of part 290 and therefrom to an image capture arrangement as shown and described above for the embodiments of FIGS. 1-3 and 5-6.

An illumination source 300, is directed to yet another embodiment of the instant invention. In this instance it consists of a first plurality of LED's 310 and a second plurality of LED's 320; each aligned to project illumination 330 and 340, respectively, towards a diffuser 350. Diffuser 350 functions in the same manner as the diffusers of the previously described embodiments wherein at least a portion of the diffused illumination is directed towards a circular surface 360 of a part, or article, 370. Illumination reflected off of circular surface of part 370 is thereafter directed to a lens and camera arrangement as described for the previous embodiments. It should be understood that alternative illumination sources such as electro luminescent strips maybe substituted for either LED's 310 or 320 or both. While two sects of illumination sources have been shown three or more may also be utilized.

While the above embodiments have been shown and described as including a housing it should be understood that a housing is not necessary for the illuminator to perform its functions. Other illumination geometry can be achieved by using fixturing to arrange and maintain the relationships between the illumination components.

The above described illuminators of the embodiments of FIGS. 5-6 and FIG. 7 also provide a uniform lighting to cover up to 180 degrees (180°) of the surface of a part such that light rays reflect off the part and back to the camera/lens combination resulting in a uniform, ("even" image. Maintaining diffused brightfield results in, 1) a high contrast between any symbology, such as a date code or data matrix (not shown) when disposed on the part surface; and 2) elimination of unwanted specular reflections. This illumination offers a wide semicircle of diffused light and can be situated just off to the side of the target or also just above the target. The image capture arrangement is to be positioned such that light is reflected to a camera at the same angle as the incident light. Because the illumination surface is wide and diffused, this angle has a degree of variability allowing some flexibility in camera positioning while still maintaining the brightfield lighting effect.

The resulting illumination will provide the widest possible solid angle of illumination, about 180° along the circumference of the part. If the distance between the illuminator and part, or other article, 70 is increased, the solid angle of illumination will decrease. This will illuminate less of the target's curved surface, but will still be suitable for certain applications.

The above described illuminators of the embodiments of FIGS. 5-6 and FIG. 7 each achieve a small footprint by virtue of its arch like shape which illuminates the target through up to 180° of its curved axis. It avoids the excess illuminated area that would be required to illuminate additional planes (e.g. cylinder ends or a spherical object). This arch shape provides a reduction in overall dimensions for illuminators designed to address targets with curved surfaces. Therefore, these illuminators also eliminate and render unnecessary items such as dual light sources, beam splitters, reflecting domes and light blocks otherwise present in conventionally available CDI's. These Illuminators rely on an assortment of LEDs or other distributed light sources placed so as to evenly project diffuse light. As the resulting diffused light illuminates the cylinder surface very evenly, any aberration of the surface by print, deposit or indentation will reflect light away from the eye of the camera and will show as a darker element along the surface. This will provide the contrast necessary for the vision algorithms to decipher the characters and or to identify imperfections. Since the camera and lens combination can be totally independent from the illumination, many different cameras and computer configurations can be used including "smart cameras".

It is understood that although there has been shown and described preferred embodiments of this invention that various modifications may be made in the details thereof without departing from the spirit as comprehended by the following claims.

What is claimed is:

1. An illuminator for diffuse illumination of a curved surface of an article, the illuminator comprising:
    a source of diffuse illumination including at least an illumination source and a diffuser coupled to the illumination source to provide diffuse illumination, the source of diffuse illumination projecting at least a portion of the diffuse illumination towards an article illumination location where a center line through the article, when so disposed, will be co-linear with an imaginary center line at which the portion of the diffuse illumination is to be directed, wherein the article illumination location is situated to the side of the source of diffuse illumination along the imaginary centerline; and
    a housing, the diffuser being disposed at a predetermined location within the housing, wherein the illumination source includes a plurality of illumination devices spaced from each other in at least a single strip-like arrangement and disposed in a semi-circular arc having an imaginary centerline that is co-linear with the center line through the article when the article is located at the article illumination location.

2. The illuminator of claim 1 wherein the illumination source is disposed within the housing at a location to project illumination through the diffuser.

3. The illuminator of claim 1 wherein the illumination source is disposed at a location to project illumination upon the diffuser to be reflected therefrom and towards an article when located at the article illumination location.

4. The illuminator of claim 1 wherein the illumination devices are light emitting diodes.

5. The illuminator of claim 1 wherein the illumination devices constitutes an electroluminescent strip.

6. The illuminator of claim 1 wherein the illumination devices are arranged in at least a pair of strips disposed parallel to each other.

7. An illuminator comprising:
a housing having on one edge thereof an arched cutout positioned between two legs;
a diffuser positioned along a contour of the arched cutout; and
an illumination source coupled with the diffuser, wherein the illumination source is disposed at a location to project illumination upon the diffuser to be reflected therefrom and toward a position substantially between the two legs.

8. The illuminator of claim 7 wherein the housing comprises a front panel with a front cutout and a rear panel with a rear cutout, wherein the contour of the arched cutout is formed by the front cutout and the rear cutout.

9. The illuminator of claim 7 wherein the contour of the arched cutout is substantially a semi-circle.

10. The illuminator of claim 7 wherein the contour of the arched cutout comprises a plurality of straight segments.

11. The illuminator of claim 7 wherein the diffuser is positioned along the contour such that the diffuser provides diffuse light substantially 180 degrees about the position between the two legs.

12. The illuminator of claim 7, further comprising an additional illumination source disposed within the housing at a location to project illumination through the diffuser.

13. A system for imaging a curved surface of an article, the system comprising:
an illuminator comprising:
a housing having on one side thereof an arched cutout positioned between two legs,
a diffuser positioned along the contour of the arched cutout, and
an illumination source coupled with the diffuser, wherein the illumination source is disposed at a location to project illumination upon the diffuser to be reflected therefrom and toward a position substantially between the two legs;
a camera disposed to receive and capture at least a portion of illumination when reflected from the curved surface when the article is positioned between the two legs; and
an image decoder disposed to decode and interpret image data captured by the camera.

14. The illuminator of claim 13 wherein the arched cutout is shaped substantially like a semi-circle.

15. The illuminator of claim 13 wherein the arched cutout comprises a plurality of straight segments.

16. The illuminator of claim 13 wherein the diffuser is positioned along the contour such that the diffuser provides diffuse light 180 degrees about the position between the two legs.

17. The illuminator of claim 13, further comprising an additional illumination source disposed within the housing at a location to project illumination through the diffuser.

* * * * *